US011576685B2

(12) United States Patent
Card et al.

(10) Patent No.: US 11,576,685 B2
(45) Date of Patent: Feb. 14, 2023

(54) DRILL GUIDE ASSEMBLY AND METHOD (71) Applicant: Medtronic PS Medical, Inc., Fort Worth, TX (US)

(72) Inventors: Jennifer Card, Fort Worth, TX (US); Brad Clayton, Superior, CO (US); Allen P. Hilton, Arlington, TX (US); John W. Kulas, Euless, TX (US)

(73) Assignee: Medtronic PS Medical, Inc., Fort Worth, TX (US)

( * ) Notice: Subject to any disclaimer, the term of this patent is extended or adjusted under 35 U.S.C. 154(b) by 101 days.

(21) Appl. No.: 17/075,546

(22) Filed: Oct. 20, 2020

(65) Prior Publication Data

US 2021/0121186 A1   Apr. 29, 2021

Related U.S. Application Data (60) Provisional application No. 62/926,010, filed on Oct. 25, 2019.

(51) Int. Cl.
*A61B 17/17* (2006.01)
*A61B 17/16* (2006.01)
*A61B 90/00* (2016.01)

(52) U.S. Cl.
CPC ...... *A61B 17/1633* (2013.01); *A61B 17/1631* (2013.01); *A61B 17/1703* (2013.01); *A61B 17/1739* (2013.01); *A61B 90/06* (2016.02); *A61B 2090/062* (2016.02)

(58) Field of Classification Search
CPC ........ A61B 2090/062; A61B 2090/034; A61B 90/06; A61B 90/11; A61B 17/1739; A61B 17/1703; A61B 2017/00991; A61B 17/17; A61B 17/1695; A61B 17/1633; A61B 17/1631; A61B 17/1622
See application file for complete search history.

(56) References Cited

U.S. PATENT DOCUMENTS

| 5,592,939 | A  | 1/1997  | Martinelli       |
| 5,772,594 | A  | 6/1998  | Barrick          |
| 5,810,828 | A  | 9/1998  | Lightman et al.  |
| 5,913,820 | A  | 6/1999  | Bladen et al.    |
| 5,983,126 | A  | 11/1999 | Wittkampf        |
| 6,940,941 | B2 | 9/2005  | Gregerson et al. |
| 7,001,045 | B2 | 2/2006  | Gregerson et al. |
| 7,001,391 | B2 | 2/2006  | Estes et al.     |
| 7,011,661 | B2 | 3/2006  | Riedel et al.    |
| 7,106,825 | B2 | 9/2006  | Gregerson et al. |
| 7,108,421 | B2 | 9/2006  | Gregerson et al. |

(Continued)

FOREIGN PATENT DOCUMENTS

WO   20190118753 A2   6/2019

OTHER PUBLICATIONS

International Search Report and Written Opinion regarding International Application No. PCT/US2020/056760 dated Feb. 22, 2021.

*Primary Examiner* — Samuel S Hanna
(74) *Attorney, Agent, or Firm* — Carter, DeLuca & Farrell LLP (57) ABSTRACT

Disclosed is a system to engage one or more tools. In the system, a drive shaft and collet may be assembled to engage and disengage, selectively, a plurality of tools. A guide may be used with the system to select various features of a procedure, such as depth and position.

18 Claims, 9 Drawing Sheets

(56) References Cited

U.S. PATENT DOCUMENTS

| | | |
|---|---|---|
| 7,188,998 B2 | 3/2007 | Gregerson et al. |
| 7,751,865 B2 | 7/2010 | Jascob et al. |
| 8,842,893 B2 | 9/2014 | Teichman et al. |
| 2004/0199072 A1 | 10/2004 | Sprouse et al. |
| 2006/0041268 A1* | 2/2006 | Shores ............... A61B 17/1633 606/180 |
| 2010/0228117 A1 | 9/2010 | Hartmann |
| 2014/0155905 A1 | 6/2014 | Keiser |
| 2017/0209154 A1 | 7/2017 | Krause et al. |

* cited by examiner

DRILL GUIDE ASSEMBLY AND METHOD

CROSS-REFERENCE TO RELATED APPLICATIONS

This application claims the benefit of U.S. Provisional Application No. 62/926,010 filed on Oct. 25, 2019. The entire disclosure of the above application is incorporated herein by reference.

FIELD

The present disclosure relates to a powered drill, and particularly to a powered drill and guide assembly.

BACKGROUND

During selected procedures, a drill motor may power a tool, such as a tool that has a tool tip or working end. For example, the tool may be rotated at a selected velocity, such as about 100 rotations per minute (RPM) to about 10,000 RPM. The tool interconnected with the motor may be connected to a drive shaft configured to be powered by the motor to rotate. A procedure may then be carried out with the tool tip while rotating when powered by the motor.

During a selected procedure, such as a surgical procedure, the user of the tool (e.g. a surgeon) may need to rely solely on visual cues and experience for determining a location of the tool tip. During the procedure, at least a working end of a tool may be hidden from direct view or complete direct view of the user. Thus, an open experience may be required to properly perform a procedure.

SUMMARY

This section provides a general summary of the disclosure, and is not a comprehensive disclosure of its full scope or all of its features.

A powered drill may be provided to perform a procedure by a user. The powered drill may be powered in any appropriate manner, such as a pneumatic power, electrical power, or other appropriate power system to rotate at selected and/or selectable speeds including about 100 RPM to about 100,000 RPM, including about 75,000 RPM. The powered drill may power a tool for performing a procedure on a selected object, such as a human patient, or other appropriate subject. The powered drill may be powered to rotate the tool, such as for drilling, forming a burr hole, or the like.

During the procedure, the subject may have a predefined location or portion for having a procedure performed thereon. For example, a skull of a patient may be selected to have a burr hole formed therein. The location, size, etc. of the burr hole may be predefined during a planning procedure. The powered drill may be operated to form the burr hole in the selected portion of the subject. Providing the powered drill to be tracked relative to an image of the subject, such as with a selected navigation system, may assist the user in determining or identifying the predetermined or selected location for performing a procedure on the subject.

A guide may be provided relative to the subject, such as the patient, for assisting in performing the procedure. The guide may interact with the powered drill for or to assist the user in guiding the tool relative to the subject. The guide may assist in determining or limiting a depth of drilling, determining a trajectory of the tool, etc.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
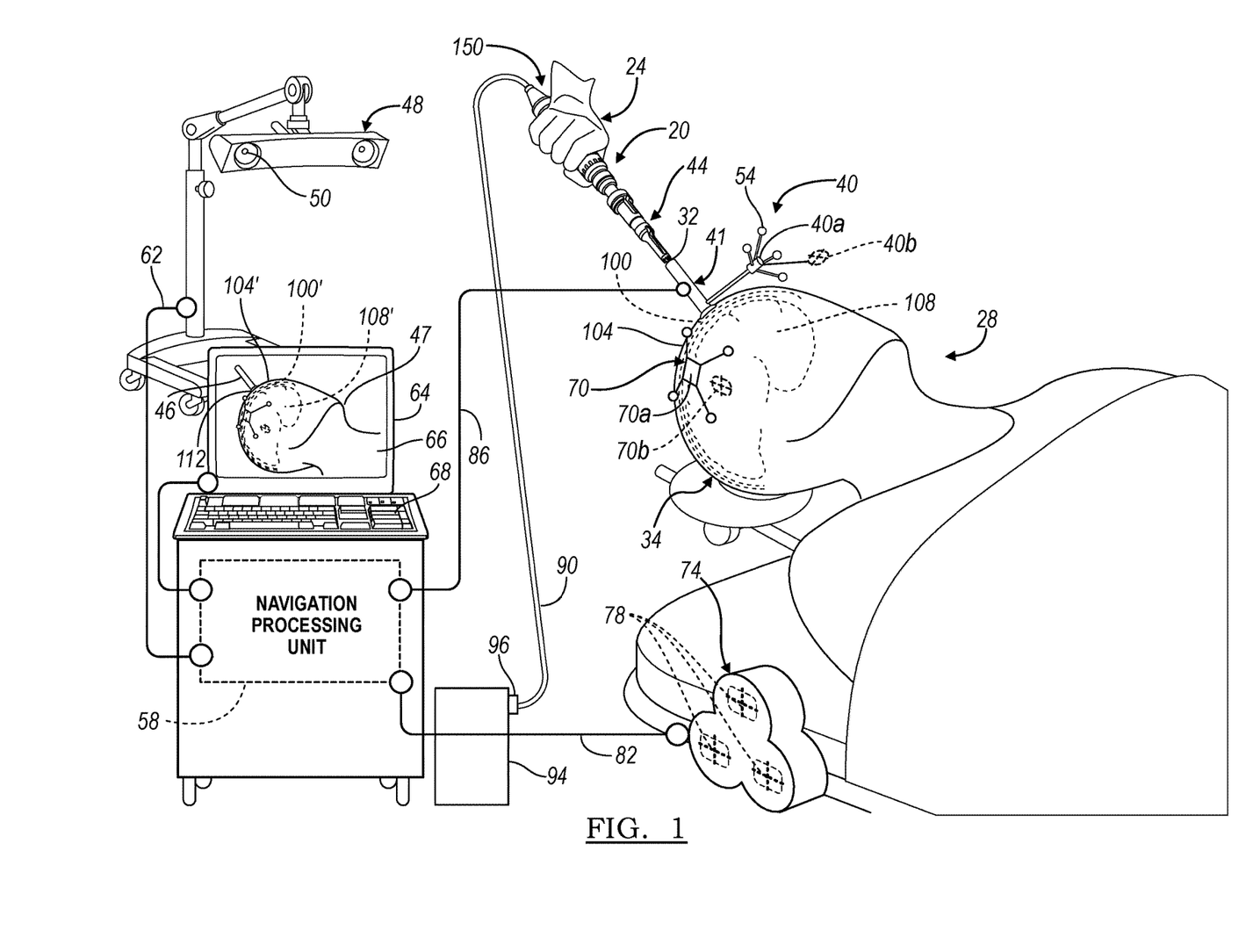
FIG. 1 is an environment view of a tracked motorized assembly.

FIG. 1 is an environmental view of an instrument, such as a powered drill assembly 20, being used by a user 24, to perform a procedure on a subject (e.g. a patient) 28. The powered drill assembly 20 may be powered to rotate a motor and/or a tool at selected and/or selectable speeds including about 100 RPM to about 100,000 RPM, including about 200 RPM to about 75,000 RPM. In various embodiments, the powered drill assembly 20 may include a tool 33 that include a working end, such as a burr 32 for performing a selected procedure, such as forming a burr hole in a cranium 34 of the patient 28. It is understood, however, that the powered drill assembly 20 may be used for performing other procedures such as a removal of material relative to a nasal cavity of the subject 28 or other appropriate procedure. Further, the powered drill assembly 20 may be used for various other procedures, including spinal procedures, orthopedic procedures, etc. For example, the powered assembly 20 may be operated to remove a portion of a vertebra in a selected procedure, including a laminectomy procedure or other appropriate spinal procedure. Various other procedures include a craniotomy, burr hole formation, etc. Further, it is understood that the powered drill assembly 20 may be used to perform a procedure on a non-living subject such as to drill a hole in an airframe, an automotive frame, or the like.

Accordingly, the powered drill assembly 20 is not required to be used with a living subject, such as a human patient.

The powered drill assembly 20 may include a motorized drill that is, in various embodiments, moveable relative to the subject 12 according to various systems and/or procedures. In various embodiments, portions or members through which the powered drill assembly 20 is moved or positioned may be tracked with selected tracking systems. For example, a tracking system, as discussed further herein, may include a tracking device 40 that may be connected to a trajectory guide 41, which may cooperate or operate with a depth guide 44, through which or relative to which the powered drill assembly 20 may more relative to the subject 28, including the cranium 34. Appropriate tracking systems include those disclosed in U.S. Pat. No. 8,842,893, incorporated herein by reference. The tracking device 40 may be any appropriate type of tracking device, include an optical tracking device 40$a$, electromagnetic tracking device 40$b$, etc.

It is understood that image data may be acquired of the subject 28 to create images, as discussed herein. To acquire the image data imaging systems (not illustrated) may be used prior to beginning a procedure or after a procedure has begun, the procedure may include operation of the powered drill 10. The imaging systems may include those disclosed in U.S. Pat. Nos. 7,188,998; 7,108,421; 7,106,825; 7,001,045; and 6,940,941; all of which are incorporated herein by reference. Other possible imaging systems can include C-arm fluoroscopic imaging systems which can also generate three-dimensional views of the patient 28.

The tracking system may be a part of a navigation system to assist in performing selected procedures, such as a surgical procedure on the subject 28, and may include those as generally known in the art. For example, navigation systems may include those as disclosed in U.S. Pat. Nos. 5,772,594; 5,913,820; 5,592,939; 5,983,126; 7,751,865; and 8,842,893 and those disclosed in U.S. Pat. App. Pub. Nos. 2004/0199072 and 2010/0228117, all incorporated herein by reference. Tracked locations may be displayed as a graphical representation 46 (e.g. an graphical representation of a tool, also referred to as an icon) on one or more images 47 (e.g. superimposed on an image) or relative to images due to registration of a location of a subject or real space to an image space, also as disclosed in the U.S. patents and publications as incorporated above. Further, tracking systems may include the Stealth Station® Trion™ tracking system, Stealth Station® Ion™ tracking system, Stealth Station® S7® tracking system, and AxiEM™ tracking system, all sold by Medtronic Navigation, Inc.

The tracking systems may include various features such as an optical tracking systems, EM tracking systems, ultrasonic tracking systems, or the like. Nevertheless, as illustrated in FIG. 1, for example, a tracking system may include one or more localizers such as an optical localizer 48 that includes one or more cameras 50 that may detect or "view" the tracking device 40. The localizer 48 including the cameras 50 may emit a selected radiation, such as infrared radiation, that is reflected by one or more trackable portions 54 that are associated with the tracking device 40. The trackable portions 54 may be viewed by the cameras 50 and a signal may be transmitted to a navigation processor unit 58. The navigation processor unit 58 may include various features, such as a navigation probe interface (NPI), as discussed further herein. The navigation processor unit 58 may also include a coil array controller (CAC) for various types of tracking systems. Various features such as the NPI, the CAC, or other portions may be provided as separate units from the navigation processor unit 58 or separate modules for interacting with various portions of the navigation system, as is generally known in the art.

Nevertheless, the localizer 48 may communicate with the navigation processor unit 58 via a selected communication line 62. The communication line 62 may be a wired or a wireless communication with the navigation processor unit 62. The navigation processor unit 58 may communicate with a selected system, such as a workstation, a terminal, or the like that includes a display system or display module 64 having a display screen 66 and one or more user inputs 58. The user inputs 54 may include a keyboard, a mouse, a touch screen, or other tactical input. Further inputs may also include a foot switch, verbal inputs, visual inputs, or the like.

The display device 64 may display one or more of the images 47 of a portion of the subject 28. The image 47 may be based on or generated with image data acquired with an imaging system as discussed above. Displayed relative to the image 47 and/or superimposed on the image 47 of the patient 28 may be the icon 46 that displays a location of the one or more tracked items, as selected, such as the guide 40. The tracked position may be determined by registering the subject 28 to a navigation space, defined by the tracking system, and tracking the tracking device 40 within the navigation space. Further, a real time position of the subject 28 may be determined with a subject tracker 70. The subject tracker 70 may be used to maintain the registration. The subject tracker may be any appropriate tracker such as an optical tracker 70$a$ and/or an EM tracking device 70$b$. Various registration and tracking techniques are known, such as those discussed above, and are not repeated here.

The tracking system may also and/or alternatively include electromagnetic tracking systems including an electromagnetic tracking array, such as a coil array 74. The coil array 74 may include one or more coil elements 78 that emit and/or receive an electromagnetic signal from an electromagnetic (EM) tracking devices such as a patient tracking device 70$b$ associated and/or connected to the patient 28 or the EM tracking device 40$b$. It is understood that various different types of tracking devices may be integrated into a single device, such as an optical array that also includes an EM coil. The coil array 74 may communicate with navigation processor unit 58 via a communication line 82 similar to the communication line 62 from the localizer device 48 to the navigation processor unit 58. Further, each of the tracking devices may communicate with the navigation processor unit 58 via selected communication lines such as communication line 86 so that a position of the selected tracking devices, including tracking device 40 and tracking device 70 may be determined with a navigation processing unit 58. It is understood that one or more than one tracking system may be used simultaneously and/or serially during the selected procedure.

The communication lines 62, 82, 86 may be a wired or wireless or other appropriate communication line. Further, it is understood that the navigation processor unit 58 may include various features such as a selected processor (e.g., an application specific integrated circuit (ASIC), general purpose processor or the like). The navigation processor unit 58 may also include a memory system (e.g. non-transitory memory systems including spinning hard disks, non-volatile solid state memory, etc.) that includes selected instructions, such as those to perform the tracking, registration, superimposing of the icon 46 on the image 47, or the like. Therefore, the determined location of the tracked member, such as with or due to the guide 41, may be displayed relative to the subject 28 by the icon 46 relative to the image 47. The user 24 may then be able to view the display device to view and/or comprehend the specific location of the tracked member subject 28 by viewing the display 64.

Figures 1A, 2:
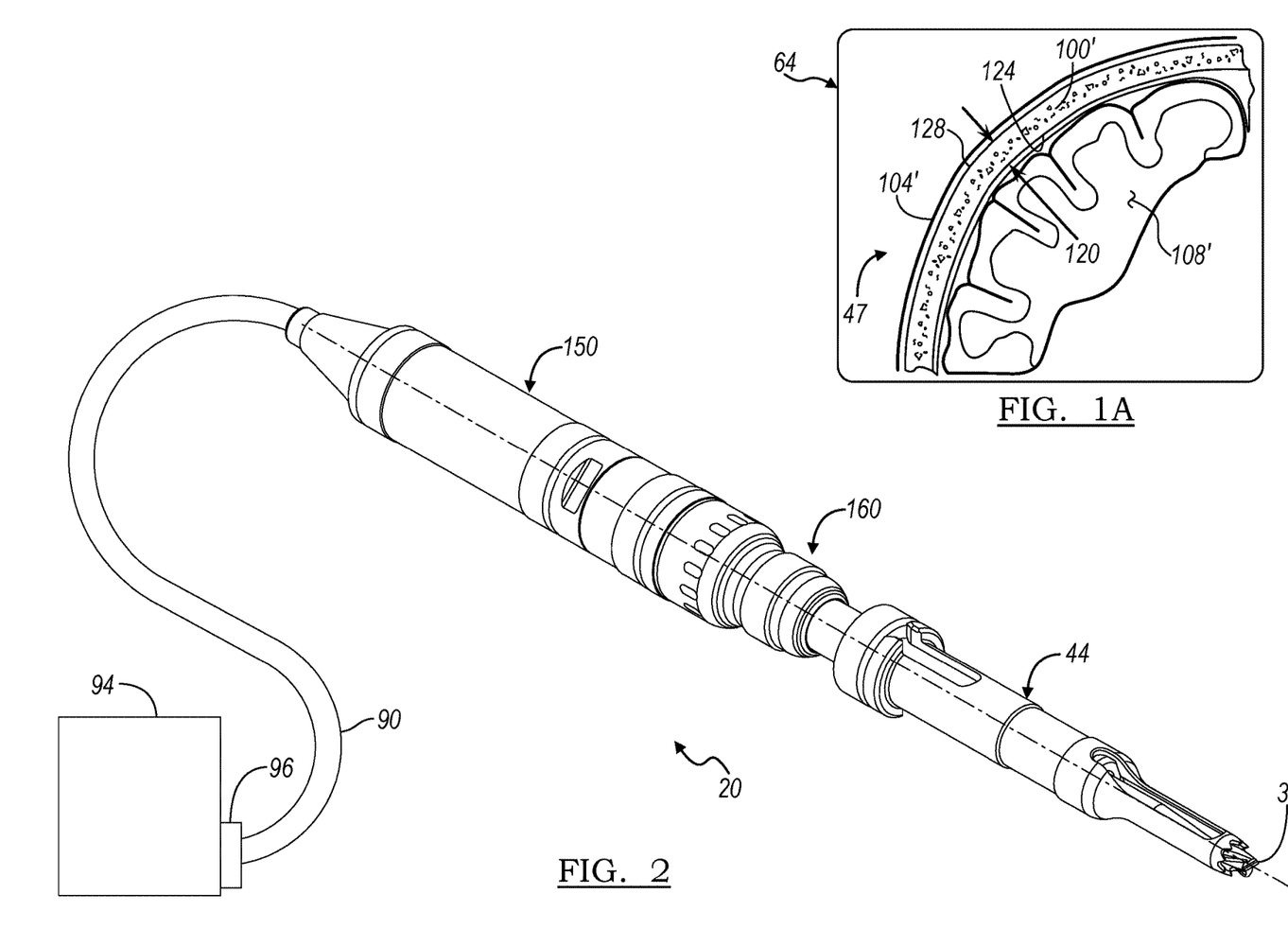
FIG. 1A is an image displayed on the display device illustrating various portions of a subject.
FIG. 2 is an assembled view of a drill motor and a depth guide assembly.

With additional reference to FIG. 2, the powered drill assembly 20 may include various components which may include a motor housing, of a motor assembly or component within the motor housing, a collet to connect a distal end to the housing, and other portions. The powered drill assembly 20 may include or include portions of powered drill assemblies including the LEGEND MR7® and/or LEGEND EHS STYLUS® motor systems, sold by Medtronic, Inc.

The power may be provided to the motor assembly via a power line 90 that is connected with a power source 94 via a connector 96. The power source 94 may be any appropriate power source such as the IPC® integrated power system, sold by Medtronic, Inc. It is understood, however, that the motor component may be any appropriate motor assembly such as one powered by electronic power, or other appropriate power supply. Therefore, the pneumatic power drill is not intended to limit the subject disclosure or the pending claims. Moreover, the motor component may include those disclosed in U.S. Pat. No. 7,011,661 or 7,001,391, both incorporated herein by reference.

Figure 3A:
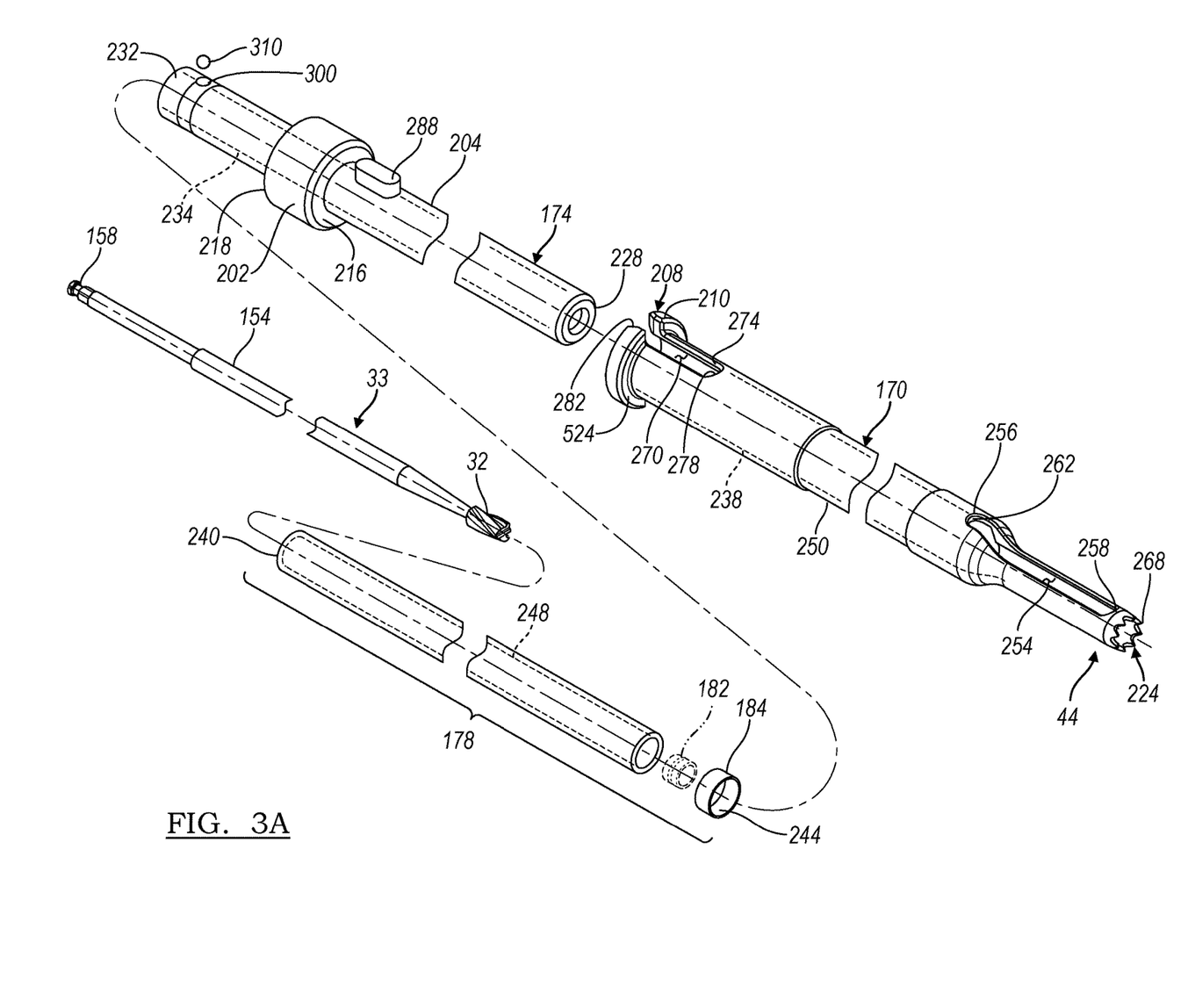
FIG. 3A is an exploded view of tube portions of a depth guide assembly, according to various embodiments.

With continuing reference to FIG. 1 and FIG. 2, and additional reference to FIG. 3, the subject 28 having the cranium 34 may be imaged, as discussed above. It is understood that any appropriate subject may be imaged, and any appropriate portion of the subject 28 may be imaged, and an image of the cranium is merely exemplary. However, with reference to FIG. 3, the cranium may be imaged and the image may be displayed for viewing by the user 24 with the display device 64, or any appropriate display device. In various embodiments, a planning procedure may occur and the planning and display device 64 may be used. The display device 64 may display all or a portion of a planning image, which may be the image 47 as discussed above, or may be a preliminary or planning image. Regardless, during planning the image 47 may illustrate or show a portion or all of a portion of the subject, such as the cranium 34.

The cranium 34, as is understood by one skilled in the art, may include a bone layer portion 100 that is covered by various tissues, such a dermis or epidermis 104 and the bone layer 100 may encompass or cover at least a portion of a brain 108. The image 47, therefore, may include images of the various portions or representations thereof, such as a bone representation 100', a dermal representation 104', and a brain tissue representation 108'.

The image 47 may be used for various purposes, such as determining positions for biopsy, placement of a deep brain simulation probe, omentectomy, or the like. In various embodiments, for example, a tumor may be identified in an image. The user 24 may use the image 47 to plan a trajectory, insertion position, and the like. For example, the user 24 may identify an entry position within an area or a region 112. The region 112 may be identified on the image 47 relative to various portions of the image 47, such as the bone layer 100'.

With reference to FIG. 1 and FIG. 1A, the image 47 may, therefore, be analyzed in the identified entry region 112 for various structures and positions, such as a thickness of the bone layer 100. In various embodiments, the user 24 may identify various portions of the image 47. Alternatively, or in addition therefore, to the processing unit 58 may execute instructions to identify various portions of the image 47. For example, the processing unit 58 may determine edges or surfaces in the image 47. In various embodiments, combinations thereof may also occur. For example, the user 24 may identify a seed pixel or voxel and the processing unit 58 may execute instructions to grow the surfaces therefrom.

In various embodiments, the image 47 may be analyzed to determine a thickness or distance 120 between two determined or defined edges, such as a first edge or surface 124 and a second edge or surface 128 of the bone 108 may be determined. The distance 120 may be measured between the two edges 124, 128. The distance 120 may be determined for selecting or assisting an appropriate procedure such as forming a borehole or bone flap through the skull, such as in the bone portion 100. As discussed further herein, forming a hole or passage that is a selected depth relative to the determined distance may assist in efficiency of a procedure, such as minimizing contact with the dural layer around the brain 108. Further the distance 120 may be used to identify or select selected depths in a depth guide, such as the depth guide 44, to assist in performing a procedure, as discussed further herein.

Figure 3B:
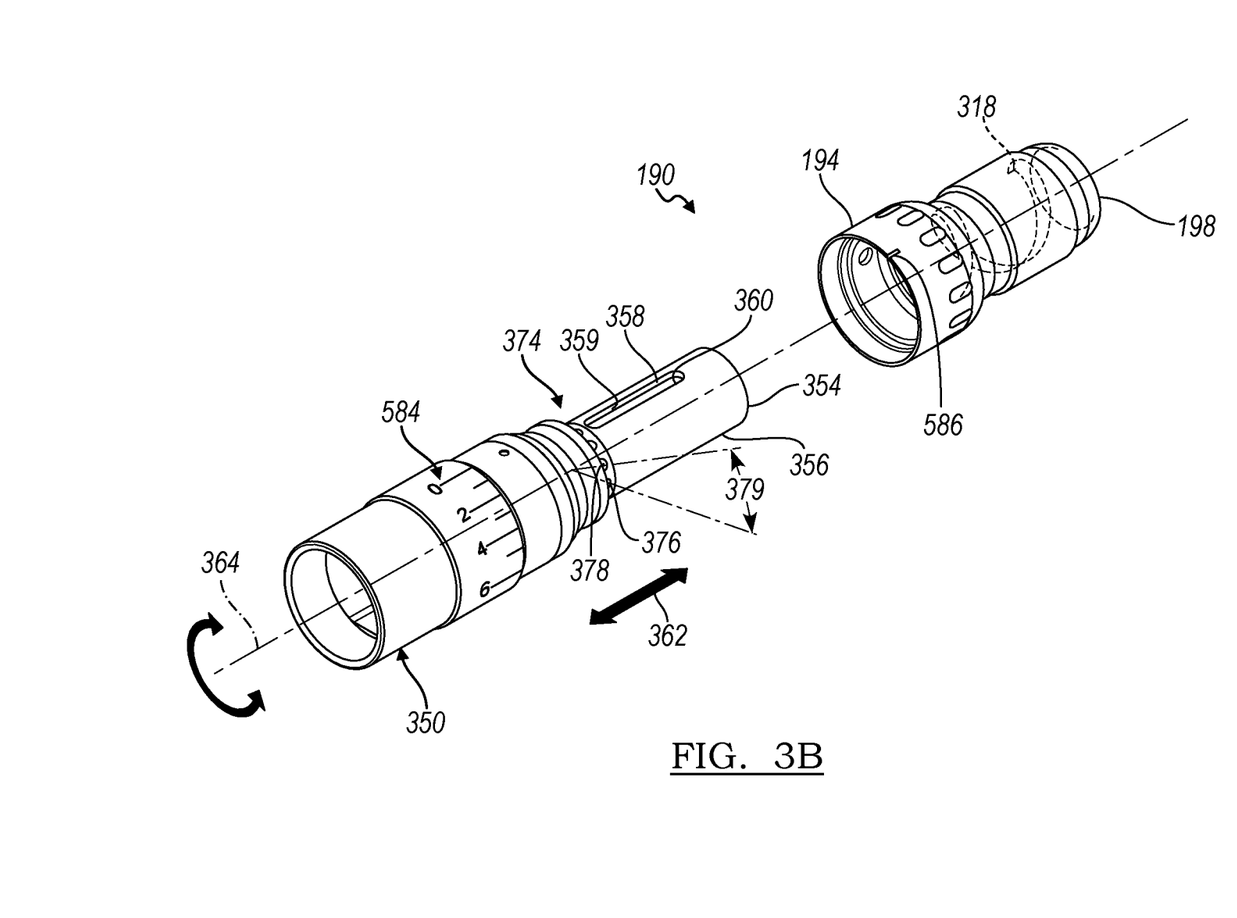
FIG. 3B is an exploded view of a collet assembly operable with the tube portions of the depth guide of FIG. 3A.

With continuing reference to FIG. 2 and additional reference to FIGS. 3A-4, the power drill assembly will be described in greater detail. The power drill assembly 20 may include various components, including those as discussed above. Generally the power source 94 may be connected to a drill motor 150. The drill motor 150 may be powered by the power source 94 in any appropriate manner, such as including an electric motor, a pneumatic motor, or other appropriate motor. Generally, the motor included within the drill motor 150 may include the motor such as that included in the Legend MR7® or Legend EHS Stylus® Motor Systems, sold by Medtronic, Inc. The drill motor 150 may be powered to rotate the burr end 32 of a tool 33 as is generally understood in the art. However, the drill motor 150 may be operated relative to the guide 44. With reference to FIG. 3, the burr 32 may include the working burr end 32 that is connected to an elongated shaft 154. The elongated shaft 154 may have a connection or coupling end 158 that connects to a portion to be driven by the drill motor 150. Accordingly, the burr 32 may rotate due to being driven by the motor 150 within the guide 44.

The guide assembly 44 may include various components that may be coupled to the drill motor 150 through a coupling or collet assembly 160, as discussed further herein. The guide assembly 44 may include various members that may be moveable relative to one another. The guide 44 may include an external or patient engaging tube or member 170, a first internal and/or intermediate tube or member 174 that may be positioned internal to the external tube 170, and an inner tube and/or bearing assembly or member 178.

The bearing assembly 178, in various embodiments, may be provided as a plurality of components that may be interconnected or coupled. In various embodiments, the bearing assembly or member 178 may include one or more race portions, for example a distal inner race 182 may be positioned within an external race portion 184. Accordingly, the shaft 154 may bear against a portion of the bearing or inner tube assembly 178. It is understood, however, that the internal or bearing assembly or member 178 may be formed as a single component or piece and/or formed as a plurality of portions or pieces that are coupled together to form the internal bearing 178. Thus, the burr 32 may be powered by the drill motor 150, through the shaft 154, to rotate the burr or distal end 32. The shaft 154 may rotate within the guide assembly 44 by at least bearing on the bearing tube or assembly 178 and rotated within the guide assembly 44.

The guide 44, as illustrated in FIG. 3A and FIG. 3B, includes a collet or drill motor connection portion 190. The collet connection portion 190, as discussed further herein, may include various motor connection portions or features such as a movable or axial slideable sleeve or member 194 that may be moved to engage and disengage a locking ball or member 324 relative to the drill motor 150. The connection of the collet assembly 190 to the drill motor 150 may include connection portions similar to those understood by one skilled in the art, such as those included with the motor assembly as discussed above.

The collet assembly 190 may further include various connection portions to interact and connect with the selected tubes or members of the guide 44, such as the intermediate tube 174 and the outer tube 170. For example, the collet 190 may include a distal end 198 that engages a stop or locking collar 202. The stop collar 202 may engage or be positioned about the intermediate tube 174, such as on an exterior surface 204 thereof. The stop collar 202 may be moved to engage a proximal end 208 of the outer tube 170. In various embodiments, the stop 202 is fixed to the intermediate tube 174 and moves with the intermediate tube 174. Thus, the stop 202 maybe fixed relative to the collet 190 at selected positions, as discussed herein.

The proximal end 208 may include a ledge or flange 210 that projects a distance and/or defines an upper surface 212 that may be engaged by the stop member or stop 202. In various embodiments, the stop 202 may include a distal end 216 and a proximal end 218. The proximal end 218 may selectively engage the distal end 198 of the collet member 190 and the distal end 216 may engage the proximal surface 212 of the flange 210. In this way, a physical barrier or stop defined by the stop collar 202 may limit an amount of movement of the collet 190 relative to the outer tube 170. In various embodiments, as discussed herein, as the collet 190 is engaged to the drill motor 150 the stop member 202 may provide a physical or mechanical stop between the drill motor 150 and the outer tube 170, such as a distal or terminal end 224 of the outer tube 170 and/or the intermediate tube 174.

The intermediate tube 174, therefore, may also define a distal end 228 and a proximal end 232. The intermediate tube 174 may define a cannula or bore 234 between the two ends 228, 232 through which the burr tool 33, including the shaft 154, may pass. Similarly, the outer tube 170 may define or form an internal bore 238 between the proximal end 208 and the distal end 224 through which the intermediate tube 174 may pass. Further the bearing tube 178 may extend between a proximal end 240 and a distal end 244 and also define an internal bore 248 therebetween. The burr tool 33 having the burr end 32 may extend through the bearing tube 178, such as through the internal bore 248, which extends or is positioned in the internal bore 234 of the intermediate tube 174, which is in turn positioned in the internal bore 238 of the outer tube 170.

In addition to the internal passages defined by the various components, the outer tube 170 may further define and/or have an exterior wall or surface 250. The exterior wall or surface may define the internal bore 238 and extend from the proximal end 208 to the distal end 224. Moreover, the external wall 250 may have one or more tracks or slots defined therethrough. For example, a first or distal slot 254 may be defined by an edge or surface 256 formed through the outer wall 250. The groove 254 may extend from a position 258 proximal from the distal end 224 and extend to a second end 262 that is distal from the proximal end 208. The groove 254 may allow for viewing of the internal bore 238 and/or position of the intermediate sleeve or tube 174 and/or the burr 32.

The outer tube 170 may further include engaging features or portions such as teeth or projections 268. The projections 268 may engage a selected portion, such as a portion of the subject 28. In various embodiments, as discussed further herein, the guide 44, including the projections 268, may engage the outer tissue 104 to engage the bone 100 and/or project into the bone 100. The projections 268 may also project into the skin or tissue 104, and not penetrate all the way to the bone 100. Nevertheless, the projections 268 may assist in holding or fixing the outer sleeve 170 in a selected position.

The outer sleeve 170 may define a second or proximal groove 270. The proximal groove 270 may be formed or defined through the outer wall 250 of the tube 170, such as with an outer edge or surface 274. The groove 270 may extend from a first end 278 that is proximal the first groove 254 and to a second end 282 which may be formed through the proximal end 208 including the flange 210. The second groove or proximal groove 270 may allow for keying or engagement of a selected keying feature, such as a key or projection member or finger 288. Thus, the intermediate sleeve 174 may engage the outer sleeve 170 in a selected orientation or manner and assist in ensuring a selected alignment of the intermediate sleeve 174 relative to the outer sleeve or tube 170.

The intermediate tube 174 may be movable relative to the collet assembly 190 due to an indent or depression 300 formed in the outer surface 204 of the tube 174, one or more connection members (e.g. a connection or interconnection sphere or ball 310 and an internal groove or track 318) formed on an interior surface of the collet 190. As discussed herein, the intermediate tube 174 may be moved relative to the collet 190 and the outer tube 170. The groove 270 and the projection 288 may allow or maintain alignment between the intermediate tube 174 and the outer tube 170 during movement.

Figure 4:
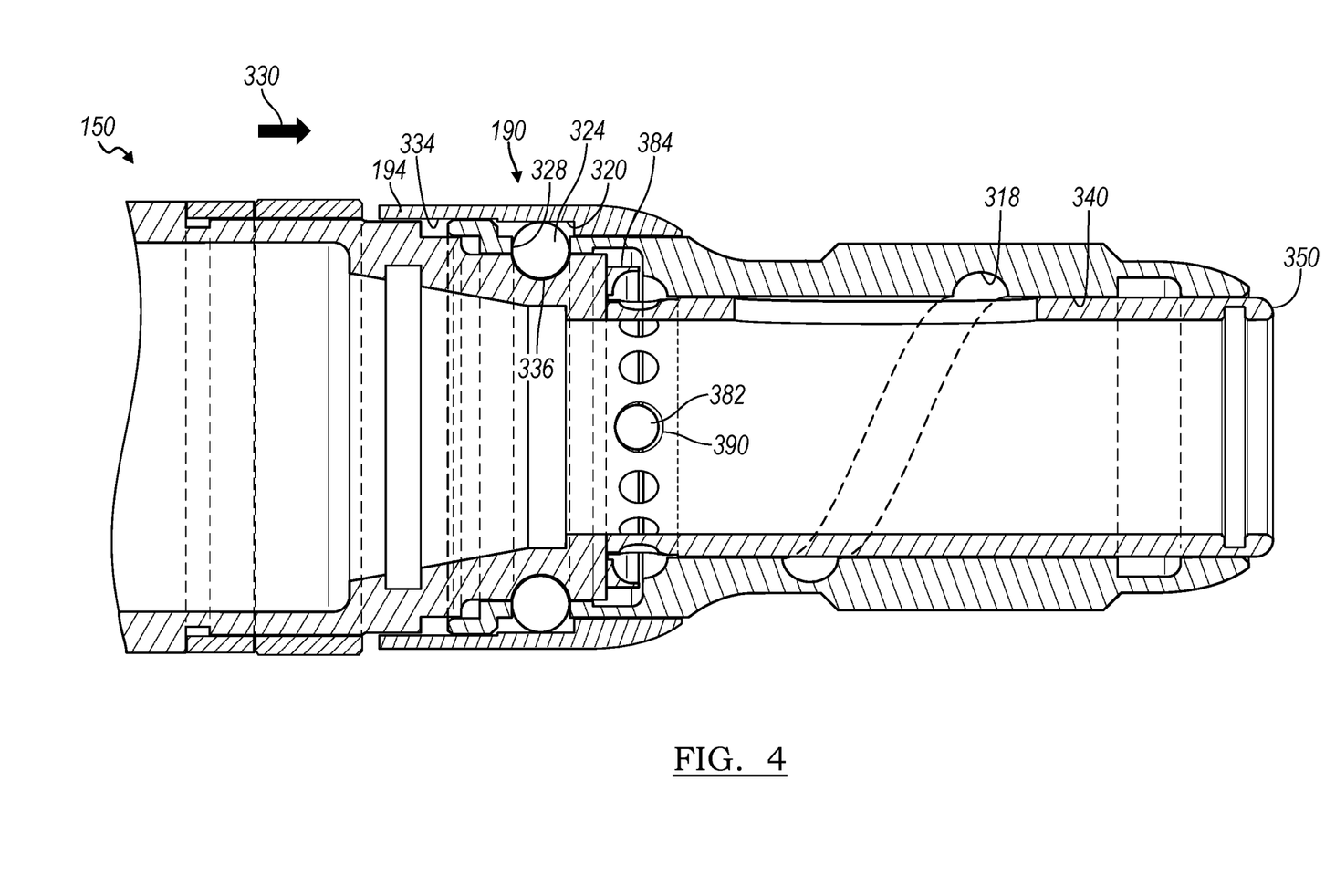
FIG. 4 is a cross-sectional view of the collet assembly of FIG. 3B.

With continuing reference to FIG. 3B and additional reference to FIG. 4, the collet assembly 190 may include the outer sleeve 194 that may have a locking or motor engaging position, as illustrated in FIG. 4, such that a first surface 320 engages a locking ball 324 through an opening or passage 328 of the collet assembly 190. In a second position, such as by sliding the sleeve 194 generally in the direction of arrow 330, a second surface 334 may allow the locking ball 324 to move away from a motor portion or motor engaging groove or indent 336. When the ball 324 moves away from the motor 150, the collet assembly 190 may be removed from the motor assembly 150. Accordingly, the user 24 or an appropriate individual may removably attach the collet assembly 190 to the motor assembly 150.

Further, the collet assembly 190 includes the internal groove 318 that forms a helical groove along a length of the collet assembly 190, such as being formed into an inner wall 340 of the collet assembly 190. Particularly, as discussed herein, the helical groove 318 may be formed in a rotatable portion 350 of the collet assembly 190. The helical groove 318 may be formed in any appropriate twist rate. For example, one full twist may equal about 0.1 millimeters (mm) to about 20 mm of axial movement, including about 5 mm of axial movement.

The helical groove 318 may receive, or at least partially receive, the engagement ball 310. The ball 310 is also received within the indent 300 of the intermediate tube 174. In various embodiments, the ball 310 is simultaneously received within the indent 300 and the helical groove 316. The intermediate tube 174 may be received within the inner or rotating portion or member 350 of the collet assembly 190. The rotating member 350 may extend through at least a portion of the collet assembly 190. Further, the rotating member 350 may include a distal end 354 having an exterior wall 356 through which a groove or channel 358 is formed.

In operation, the ball 310 with the various portions, including the rotatable member 350 and the grooves and indents may form a selection system or selector (e.g. an axial or rotational position selector or positioner). The channel 358 may allow the ball 310 to be partially received within the indent 300 and within the groove 318. The ball 310 may move along a length of the groove 358, thus allowing generally axial movement of the intermediate tube 174, such as generally in the direction of the double headed arrow 362 along or in line with a longitudinal axis 364. The rotating member 350 may be rotated around the longitudinal axis 364 such as generally in the direction of the double headed arrow 368. Due to the ball 310 being held in the groove 358, the ball 310 may move along the helical groove 318 formed into the surface 340 of the collet assembly 190. As discussed further, herein due to the balls at least partial capture within the indent 300 of the intermediate tube 174, the intermediate tube 174 may also move generally axially, such as along the axis or in line with the axis 364 generally in the direction of the double headed arrow 362 during rotation of the rotatable member 350.

Further the rotatable member 350 may include a haptic engagement region or portion 374 that may include a plurality of indents, such as an indent 376 and an indent 378. Any selected number of indents may be formed in the haptic feedback region 374. The haptic feedback region 374 may allow for movement and holding (e.g. locking) of the rotatable member 350 relative to an exterior portion of the collet assembly 190 to maintain a selected position of the intermediate tube 174. For example, the haptic feedback region may have the indents 376, 378 evenly spaced at about 0.1 mm to about 20 mm, including about 5 mm apart. Also, a selected number of the indents may be formed around the rotatable member 350, such as about 5 to about 50, including about 20 (i.e. a selected angle 379 apart, e.g. about 18 degrees apart). Thus, in various embodiments, 20 engagements and disengagements (e.g. increments) may be formed in one full rotation of the rotatable member 350. In other words, 20 increments may be used and/or felt by the user 24 to make one full rotation of the rotatable member 350. This allows the rotatable member 350 to create or allow incremental rotation and, therefore, axial movement of the intermediate tube 174. Each increment of rotation equals one selected amount of axial movement, when the twist rate of the groove 318 is constant and the indents are all equally spaced apart around the rotatable member 350.

The indents of the haptic feedback region 374 may also at least partially receive one or more engagement or holding members, such as ball 382. The ball 382 may be held between a ball holding member 384. The ball holding member 384 may apply a biasing force on the ball 382, in various embodiments. For example, the ball holding member 384 may be formed of a deformably resilient material. In various embodiments, a biasing member may be used to hold the ball holding member 384 against the ball 382 to bias the ball 382 in a selected position, such as within at least one of the indents in the haptic region 374.

Further, the ball 382 may be held within an indent or depression 390. The ball holding member 384 may allow for a selected amount of movement of the ball 384 from within the haptic feedback region 374 to allow the rotating member 350 to rotate around the longitudinal axis 364, such as in the direction of the double headed arrow 368. During rotation of the rotatable member 350 the holding member 384 may allow the ball 382 to rise out of a selected depression, such as the first depression 376, and move to a selected different depression, such as the second depression 378. Movement of the ball 382 in and out of the respective depressions 376, 378 may provide a selected haptic and/or audible feedback to a user, such as the user 24, during rotation or movement of the rotatable member 350.

Rotation of the rotatable member 350 allows rotation of rotation member 350, including a distal end 354 defining the groove 358. The holding or adjustment ball 310 may be engaged or contacted by a portion of the groove 358, such as a first edge 359 when rotating the rotatable member 350 in a first direction or a second edge 360 when rotating the rotatable member in a second direction. When engaging the ball 310 the respective edges 359, 360 may move the ball 310 due to rotation of the rotatable member 350. As discussed above, the ball 310 is at least partially received within the helical groove 318. Accordingly, the ball may move along the helical groove 318 causing an axial movement of the intermediate tube 174, as the ball 310 is also at least partially received within the indent 300. Thus, the rotatable member 350 may allow rotation of the ball 310 in the groove 318 and axial movement of the intermediate tube 174.

The rotatable member 350 may be engaged and moved by engaging the collet assembly 190. Nevertheless, after rotation of the rotatable member 350, the holding ball 382 may engage within a selected depression, such as the second depression 378 of the haptic feedback region 374 to hold the rotatable member 350 in a selected rotational position. Thus, the axial position of the intermediate tube 174 relative to the collet 190 may be selected and maintained due to interaction of the holding ball 382 in a selected one of the indents of the haptic feedback region 374 and the indent or depression 300 of the intermediate tube.

In various embodiments, the intermediate tube 174 may also or alternatively define or engage the ball 310 in a helical groove (similar to the groove 318) formed in the outer surface 204 of the intermediate tube 174. The groove 318 formed in the collet assembly 190 may be a substantially elongated groove and/or a single depression. Accordingly, the groove and depression configuration may be reversed relative to the intermediate tube 174 and the collet assembly 190, while still maintaining the operation of the collet assembly 190 to move the intermediate tube 174 relative to the motor assembly 150 and/or a selected portion of the collet assembly, such as the haptic feedback region 374.

Figure 5:
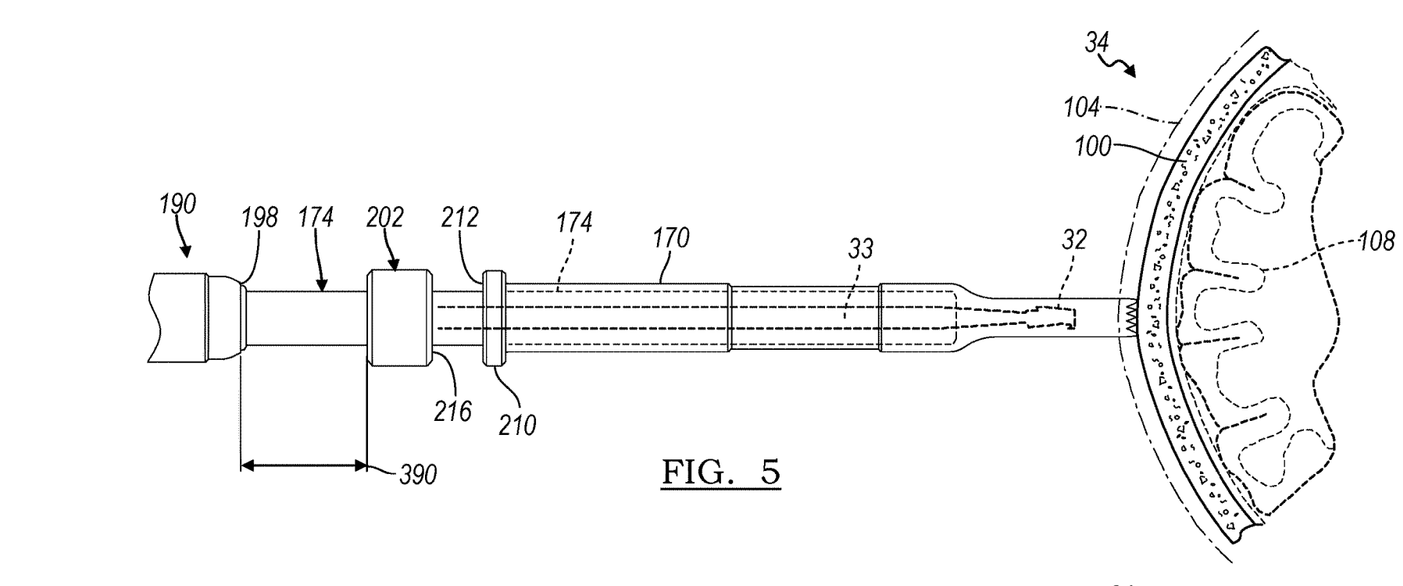
FIG. 5 is an environmental view of a depth guide and collet assembly in a first configuration in a first position.
Figure 6:
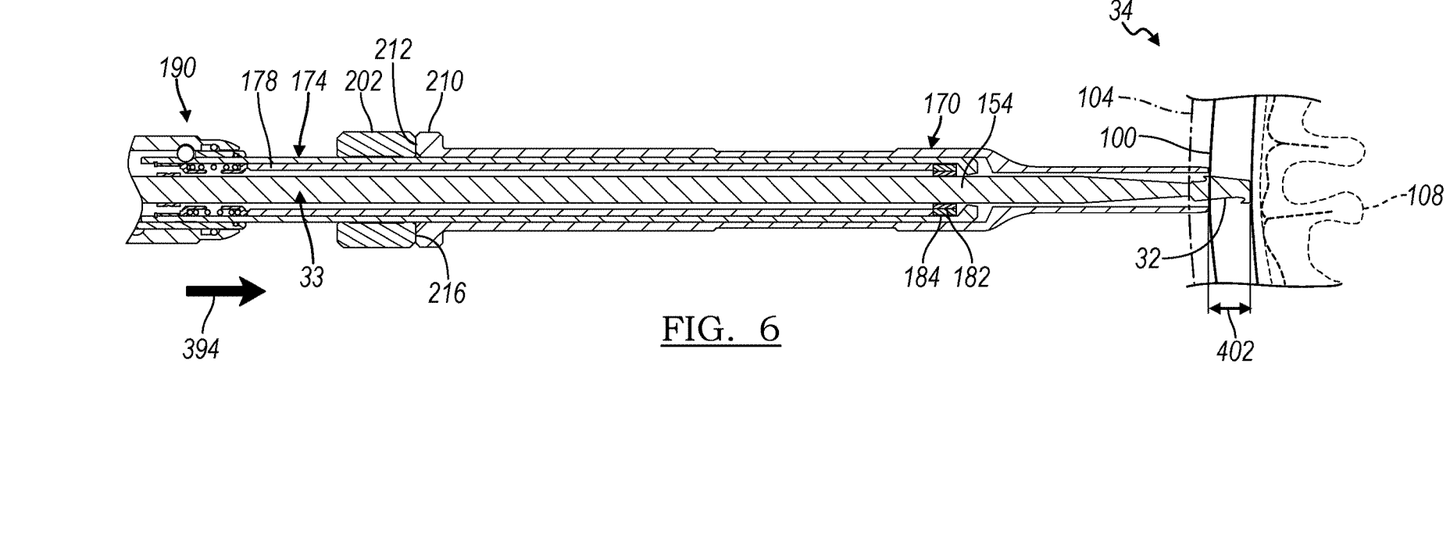
FIG. 6 is an environmental view of the depth guide in the first configuration in a second position.

With continuing reference to FIGS. 1-4 and additional reference to FIGS. 5 and 6, the drill motor assembly 20 may be operated relative to the cranium 34. As illustrated in FIG. 5, the outer tube 170 may engage the bone 100, such as through piercing, stab, or puncture of the tissue 104. The collet assembly 190 may be operated to position the intermediate tube 174 such that the stop 202 is a selected first distance 390 from the distal end 198 of the collet assembly 190. In a non-operating position, therefore, the burr 32 is positioned a distance from the bone 100 and the stop 202, such as in a disengaging end 216 is not engaging the top end or surface 212.

With continuing reference to FIG. 5 and additional reference to FIG. 6, however, the drill motor 150 may be operated to rotate the burr 32. During operation of the burr 32, the collet assembly 190 may be moved generally in the direction of arrow 394 toward the bone 100. The stop 202 may engage the stop surface 212 of the flange 210 of the outer tube 174. By engaging the flange 210 the burr 32 may stop or extend only a selected distance, such as a drill or burring distance 402, which is a distance beyond the distal end 224 of the outer tube 170. The distance 402 may be less than a distance through the bone 100, such as without engaging the brain 108.

The distance 402 may be determined in any appropriate manner such as with image analysis, manual manipulation analysis, or the like of the subject 28. Nevertheless, the distance 390 of the stop 202 from the distal end 198 of the collet assembly 190 may be determined to ensure that the distance 402 that the burr 32 extends from the outer tube 170 does not engage selected areas or tissues, such as the brain 108.

Figure 7:
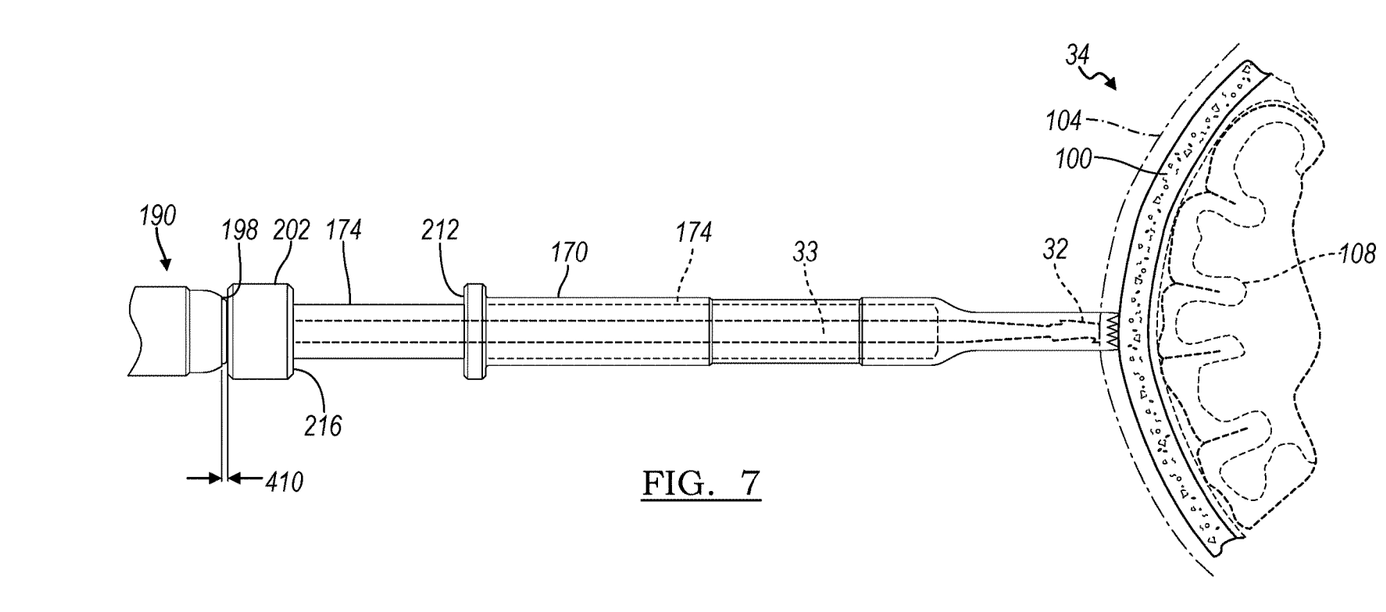
FIG. 7 is an environmental view of the depth guide in a second configuration in a first position.
Figure 8:
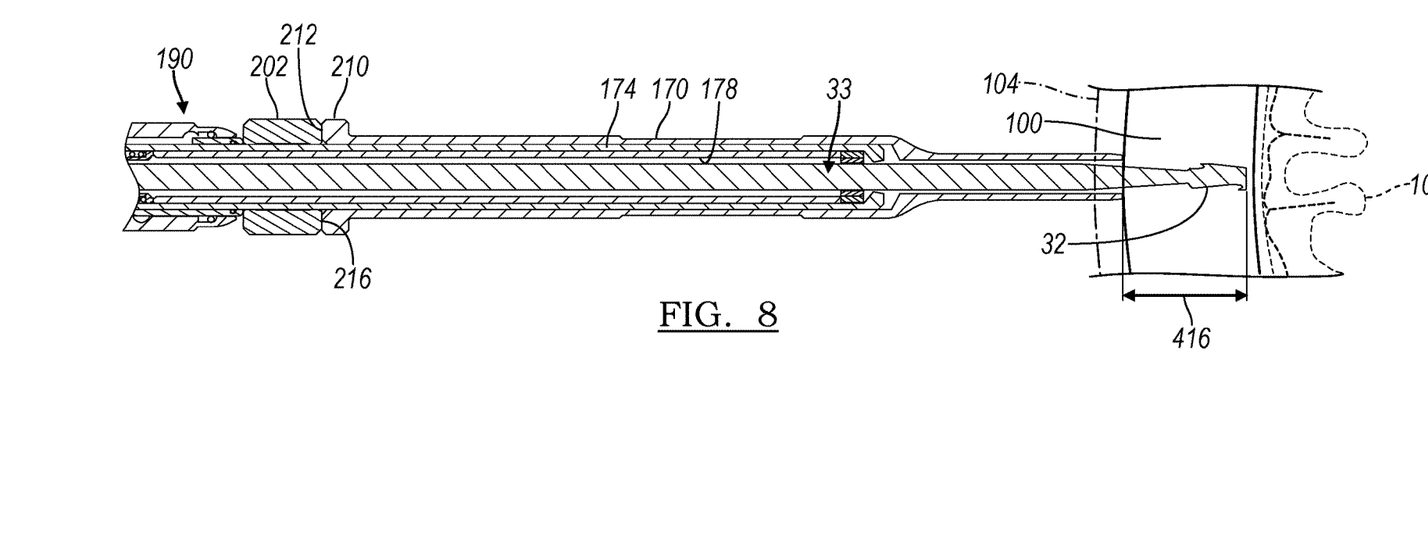
FIG. 8 is an environmental view of the depth guide assembly in the second configuration in a second position.

As discussed above, the collet assembly 190 may allow for axial movement of the intermediate tube 174. Axial movement of the intermediate tube 174 may allow for positioning the stop member 202 at a second distance 410, as illustrated in FIGS. 7 and 8. The distance 410 may be less than the distance 390, such as by rotating the rotatable member 350 to move the adjustment ball 310 in the helical groove 318, thereby moving the intermediate tube 174. The stop 202, therefore, may be positioned at a selected second distance, such as the second distance 410 from the distal end 198 of the collet assembly 190. Accordingly, the stop member may be positioned closer to the collet assembly 190 such that the burr 32 extends a greater distance from the collet assembly 190. Thus, the burr member 32 may extend a second burr extension distance 416 from the distal end 224 of the outer tube 170. The second burr extension distance 416 may also be determined through any appropriate analysis, such as that discussed above. Nevertheless, once the stop 202, such as the stop edge or end 216 engages the stop engaging surface 212 of the flange 210 the burr portion 32 is stopped in advancement relative to the outer tube 170.

Accordingly, the collet assembly 190 allows for positioning of the stop member 202 relative to the collet assembly 190. By positioning the stop member 202 relative to the collet assembly 190, the projection distance of the burr 32, such as the first projection distance or extension distance 402 and the second extension distance 416, may be achieved. The extension distances 402, 416 may be any appropriate extension distances and may be determined by rotating the rotatable member 350 relative to the collet assembly 190. One skilled in the art understands that the two extension distances 402, 416 are merely exemplary and not intended to limit the extension distances and/or the number of extension distances achievable. As discussed above, the collet assembly 190, however, includes the haptic feedback portion 374 to allow for a haptic and/or audible feedback to the user 24 when a position is selected and any number of selected positions and/or distances. Further, the stop 202 provides mechanical and physical stop for a distance of the burr 32 extending from the outer tube 170.

Figure 9:
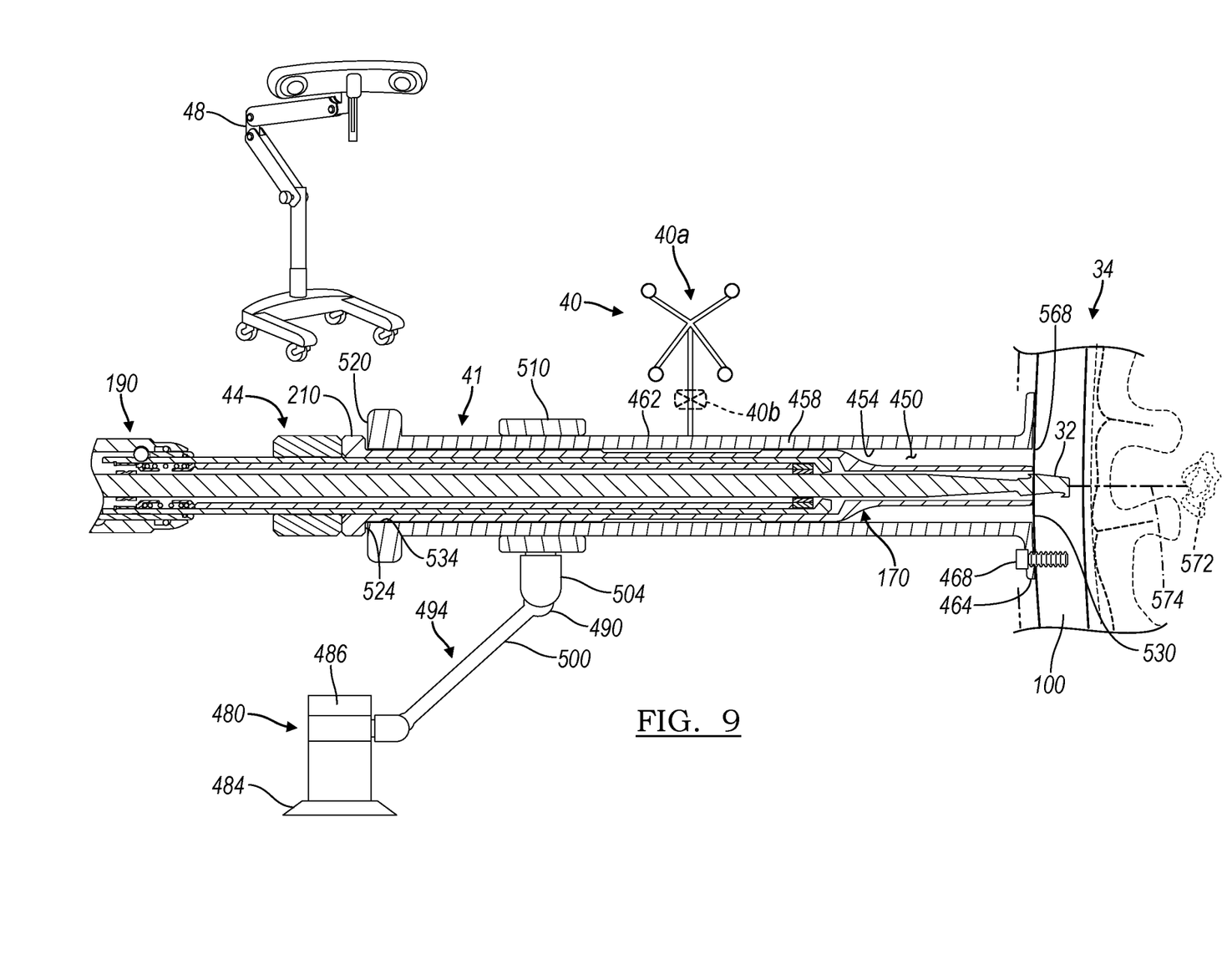
FIG. 9 is an environmental view of the depth guide assembly with a trajectory guide.

As discussed above, the depth guide assembly 44 may be used to assist in determining a depth of a burr hole or bore. The depth guide 44, when connected with the drill motor 150, may be moved relative to the cranium 34 of the subject 28. In various embodiments, as discussed above, the trajectory guide 41 may be used in combination with the depth guide 44. In particular, the depth guide 44 may be passed through an internal bore 450, as illustrated in FIG. 9.

The guide tube 41 may have an internal bore 450 that is defined by an internal wall or surface 454. The guide tube 41 may, therefore, include a body 458 that includes or defines the internal wall 454 and an external wall 462. The internal bore 450 may include a selected fit or engagement with an outer surface of the outer tube 170. Thus, the guide tube 41 may be used to guide the depth guide 44 relative to the cranium 34. With continuing reference to FIG. 9, the guide tube 41 may be positioned relative to the cranium 34, such as in contact with a bone surface 100 thereof.

In various embodiments, the guide tube 41 may include an engagement surface or portion 464. The engagement surface or portion may include fixation members 468. The fixation member 468 may be any appropriate fixation or mechanical connection member, such as a screw, bolt, rivet, or the like. It is understood that other appropriate fixation mechanisms may also be used such as an adhesive or other portion to interconnect the guide 41 to the cranium 34.

The guide 41 may be positioned relative to the cranium 34 in an appropriate location to guide or track a trajectory of the burr 32 prior to and/or during forming a burr hole or bore into the bone 100 of the subject 28. The trajectory guide 41 may be tracked with the tracking device 40, as discussed above. The tracking device 40 may be any appropriate tracking device and may be connected to the guide 41 in any appropriate manner, such as with a clamp, screw, or the like. It is understood that the tracking device 40 may be removably attached to the guide 41 and/or integrated with the guide 41.

In various embodiments, the guide 41 may in addition to and/or alternatively to the tracking device 40 be held and/or tracked with an automatic (e.g. robotic) system 480. The robotic system 480 may be mounted to a selected surface 484, such as a floor, table, or the like. Nevertheless, the surface 484 and/or a body 486 of the robotic system 480 may be used as an origin point. One or more joints 490 may allow for movement of an arm portion 494 relative to the robotic origin 486. The robotic arm 494 may include a first arm portion 500 and a second arm portion 504 interconnected at the joint 490. The guide tube 41 may be held with a selected clamp or connection portion 510. The robotic system 480 may move the guide tube 41 relative to a selected location relative to the cranium 34 to position the guide tube 41 to guide the trajectory of the burr 32 through the trajectory guide tube 41.

As illustrated in FIG. 9, the trajectory guide tube 41 may be positioned and/or tracked relative to the cranium 34. The depth guide 44 may then engage the guide tube 41, such as within the internal wall 454, as illustrated in FIG. 9. Further, the depth guide 44 may pass a selected depth through the trajectory guide 41 and engage an upper surface or flange 520 with a lower surface or flange surface 524 of the flange 210. Thus, the depth guide 44 may be positioned at a selected and/or known depth relative to the guide tube 41. In various embodiments, the length of the guide tube 41, such as between a first end 530 and a second end 534 may be substantially equivalent to a distance or length of the outer tube 170 from the distal end 224 to the proximal end 208 and/or the flange engaging surface 524. Thus, the outer guide tube 170 may define a relative depth or travel position for the burr 32 when determining or identifying a depth for forming the burr hole into the subject 28. Accordingly, the guide tube 41 may be used in concert with the depth guide 44 to track and/or determine or confirm a trajectory of the depth guide 44 relative to the subject 28.

With continuing reference to FIG. 1 and FIG. 9, the depth guide 44 may be used with or without the guide tube 41 in a selected procedure. With additional reference to FIG. 10, a procedure may proceed according to various embodiments, including a process 550. Generally, the process 550 may start in start block 554. After the start block 554, accessing subject data may occur in block 558. The accessing subject data in block 558 may be accessing any appropriate subject data, such as image data, manual manipulation, prior medical history, or the like. The accessing of a subject data may be performed with the processor system 58, as discussed above. For example, image data may be accessed and/or acquired and analyzed with the processing unit 58.

Figure 10:
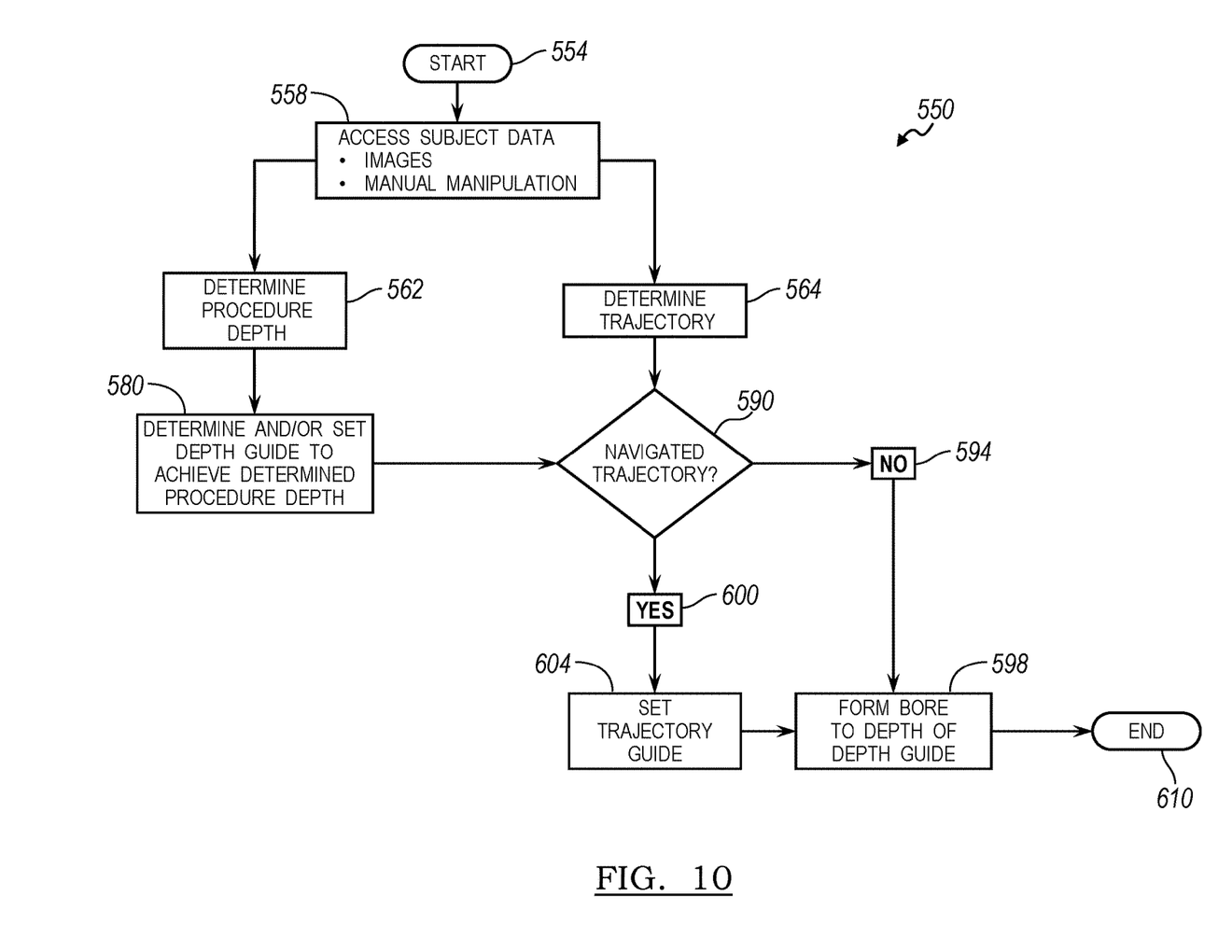
FIG. 10 is a flow chart of a method.

After accessing the subject data in block 558, determining a procedure depth may be determined or created in block 562. Determining a procedure depth may include analyzing image data of the subject to determine the thickness 120 of the bone 100 and/or a distance to a selected critical or determined tissue, such as the brain 108. The depth may be any appropriate depth and may be determined based upon analysis of the image data or other appropriate data. In various embodiments, for example, the image data may be analyzed with the processor unit 58 that executes instructions to determine surfaces and/or edges. Edges of the bone 100 may be determined and a distance or depth between the edges, such as the distance 120 may be determined. The determined depth may be made in block 562.

After determining the depth of the procedure in block 562 and/or in tandem with determining the depth of the procedure in block 562, determining a trajectory in block 564 may occur. Determining the trajectory in block 564 may include determining an entry point, a target, and a path therebetween. Determining the trajectory may also include determining an angle of the depth guide 44 to achieve the selected trajectory. Determining the trajectory in block 564 may include appropriate procedures such as planning a path, including a straight path, from the entry point, such as an entry point 568 (see FIG. 9) to a target 572. A trajectory 574 may include a straight path from the entry point 568 to the target 572. Accordingly, determining a depth and determining a trajectory may be made before using the depth guide 44.

After determining the procedure depth in block 562, setting the depth guide 44 to achieve the determined procedure depth may be made in block 580. The depth guide 44 may be adjusted, as discussed above. For example, the collet 190 may be rotated and the user 24 may use feedback from the haptic feedback region 374 to achieve a selected depth. Various demarcations may be included on the collet assembly 190, such as in a scale 584 (see FIG. 3B) on the rotatable portion 350 and a marker or marking 586 on the sleeve 194. The sleeve 194 may be fixed at a selected rotational position relative to the collet assembly 190 therefore rotating the rotatable portion 350 may rotate the scale 584 relative to the mark 586. Thus, the protruding depth or length may be read from the marking 584. It is understood that the depth may also be tested by pressing the depth guide 44 when attached to the drill motor 150 into a dummy or test rig. Nevertheless, the depth may be set in block 580.

Once the depth guide 44 is set in block 580, a determination of whether the trajectory will be navigated in block 590 may be made. Determining whether navigation of the trajectory is made in block 590 may be used to determine whether the guide 41 and/or the robotic system 480 may be used to guide a trajectory of the guide tube 44 relative to the cranium 34. If it is determined that no navigation is used, a NO path 594 may be followed to form a bore in block 598. The bore may be formed with the depth guide 44, as discussed above, after setting the depth guide and pressing the burr 32 through the depth guide 44. The trajectory may be manually determined and/or achieved by use of the user 24, or other appropriate manual manipulation.

If navigation is used, a YES path 600 may be followed to a set trajectory guide in block 604. As discussed above, setting the trajectory guide 41 may be used or performed in any appropriate manner such as with the tracking device 44 and/or the robotic system 480. Nevertheless, the trajectory guide 41 may be tracked to determine that the determined trajectory 564 is achieved and/or to position the trajectory guide 41 at the determined trajectory from block 564. Accordingly, the trajectory guide 41 may be tracked and/or set to achieve the determined trajectory. After the trajectory guide is set in block 604 the bore may be formed in block 598. The bore may be formed in block 598 with the set trajectory guide from block 604 in a manner similar to that discussed above.

After forming the bore in block 598, either with or without navigation, a procedure may end in block 610. Accordingly, the process 550 may allow for forming a bore with the depth guide 44 after setting the depth guide to an appropriate depth. The appropriate depth may be determined based upon analysis of subject data, such as image data of the subject 28. Regardless, the depth guide 44 may be used to select a depth of the burr hole formed by the burr 32 in the subject, such as in the cranium bone 100.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An instrument assembly for selecting a protrusion, comprising:
   a first tube having a first wall extending from a first terminal end to a second terminal end, wherein the wall has a first inner surface that defines a cannula extending through the first terminal end to and through the second terminal end;
   a second tube having a second wall extending from a third terminal end to a fourth terminal end, wherein the second wall has a second inner surface that defines a cannula extending through the third terminal end to and through the fourth terminal end;

a stop member fixable at a selected position between the third terminal end and the fourth terminal end, wherein the stop member is operable to selectively engage the second terminal end of the first tube;
a collet assembly, comprising:
an outer tube extending from a fifth terminal end to a sixth terminal end,
an inner tube extending from a seventh terminal end to an eighth terminal end, wherein the inner tube is at least partially received within and rotatable within the outer tube,
a rotation position selector having a selection member positionable in at least one indent of a plurality of indents within the inner tube and a holding member to bias the selection member within the at least one indent;
a second tube position selection system comprising a second tube holding member operable to be received within at least a first portion of an outer surface of the second wall and a second portion of an inner surface of the outer tube;
wherein rotation of the inner tube of the collet assembly is operable to axially move the second tube and the stop member relative to the outer tube of the collet assembly.

2. The instrument assembly of claim 1, wherein the second tube holding member is simultaneously received within the first portion of the outer surface of the second wall and the second portion of the inner surface of the outer tube.

3. The instrument assembly of claim 1, wherein the first portion of the outer surface of the second wall includes an indent.

4. The instrument assembly of claim 1, wherein the second portion of the inner surface of the outer tube includes a helical groove extending around the inner surface and at least a selected distance between the fifth terminal end and the sixth terminal end.

5. The instrument assembly of claim 1, wherein the selection member includes a ball operable to move between the plurality of indents based upon a rotational position of the inner tube relative to the outer tube.

6. The instrument assembly of claim 1, wherein the plurality of indents are formed around a circumference of the inner tube.

7. The instrument assembly of claim 1, wherein the rotation position selector further comprises a groove formed in the inner tube extending at least a portion of a distance between the seventh terminal end and the eighth terminal end;
wherein the groove is operable to engage the second tube holding member and move the second tube holding member upon rotation of the inner tube.

8. The instrument assembly of claim 7, wherein the second tube holding member is a ball.

9. The instrument assembly of claim 1, further comprising:
an inner bearing member received within the second cannula.

10. The instrument assembly of claim 1, further comprising:
a tool having a shaft and a working end;
wherein at least the shaft of the tool is operable to bear on the inner bearing within the second tube;
wherein the tool is operable to rotate and move axially within the inner bearing within the second tube.

11. The instrument assembly of claim 1, wherein the wall of the outer tube further defines a first groove extending through the wall at the first terminal end open to the cannula.

12. The instrument assembly of claim 1, wherein the wall of the outer tube further defines a second groove extending through the wall at the second terminal end open to the cannula;
wherein the groove is formed through the second terminal end of the wall and operable to receive a member within the second groove.

13. An instrument assembly for selecting a protrusion, comprising:
a first tube extending between a first terminal end and a second terminal end, wherein the first tube has a first tube indent;
a stop member fixed at a selected position on the first tube; and
a collet assembly having a distal end, wherein the stop is operable to be held at a selected position relative to the distal end with an axial position selector comprising:
an outer tube having an inner surface with a helical groove formed therein,
an inner tube having a plurality of indents formed near a first inner tube end and an axial groove formed near a second inner tube end, wherein the inner tube rotatable within the outer tube,
a rotation selection ball operable to be moved between selected indents of the plurality of indents, and
a first tube axial selection ball received within the first tube indent and the helical groove and operable to be engaged by at least a portion of the axial groove to move the first tube axial selection ball;
wherein rotation of the inner tube of the collet assembly is operable to axially move the first tube and the stop member relative to the outer tube of the collet assembly.

14. The instrument assembly of claim 13, further comprising:
a second tube extending between a third terminal end and a fourth terminal end;
wherein the first tube is operable to be received within the second tube.

15. The instrument assembly of claim 14, wherein the stop member is operable to engage an end of the second tube.

16. The instrument assembly of claim 15, further comprising:
a rotation selection ball biasing member configured to bias the rotation selection ball within a selected one of the indents of the plurality of indents.

17. The instrument assembly of claim 16, wherein each indent of the plurality of indents relates to an axial position of the stop member relative to the distal end of the collet assembly.

18. The instrument assembly of claim 16, wherein the rotation selection ball provides haptic feedback to a user when at least one of moving from the selected indent, engaging the selected indent, or combinations thereof.

* * * * *